US007317113B2

(12) United States Patent
Bombardelli et al.

(10) Patent No.: US 7,317,113 B2
(45) Date of Patent: *Jan. 8, 2008

(54) PROCESS FOR THE PREPARATION OF THE 14β-HYDROXY-BACCATIN III-1,14-CARBONATE

(75) Inventors: Ezio Bombardelli, Milan (IT); Gabriele Fontana, Milan (IT); Arturo Battaglia, Bologna (IT); Andrea Guerrini, Bologna (IT); Eleonora Baldelli, Bologna (IT)

(73) Assignee: Indena S.p.A., Milan (IT)

( * ) Notice: Subject to any disclaimer, the term of this patent is extended or adjusted under 35 U.S.C. 154(b) by 360 days.

This patent is subject to a terminal disclaimer.

(21) Appl. No.: 10/492,589

(22) PCT Filed: Jul. 15, 2002

(86) PCT No.: PCT/EP02/08007

§ 371 (c)(1),
(2), (4) Date: Sep. 14, 2004

(87) PCT Pub. No.: WO03/035634

PCT Pub. Date: May 1, 2003

(65) Prior Publication Data

US 2005/0020669 A1  Jan. 27, 2005

(30) Foreign Application Priority Data

Oct. 19, 2001 (IT) ............... MI2001A2185

(51) Int. Cl.
*C07D 301/27* (2006.01)
*C07D 307/77* (2006.01)
*C07D 407/00* (2006.01)

(52) U.S. Cl. ............... 549/297; 549/510; 549/511; 549/514

(58) Field of Classification Search ............... 549/510, 549/511, 514, 297
See application file for complete search history.

(56) References Cited

U.S. PATENT DOCUMENTS

| 5,705,508 | A | 1/1998 | Ojima et al. | |
|---|---|---|---|---|
| 6,768,012 | B2 * | 7/2004 | Battaglia et al. | 549/510 |
| 7,078,432 | B2 * | 7/2006 | Bombardelli et al. | 514/449 |
| 7,078,538 | B2 * | 7/2006 | Pontiroli et al. | 549/214 |
| 2004/0014998 | A1 * | 1/2004 | Pontiroli et al. | 549/510 |
| 2004/0030164 | A1 * | 2/2004 | Pontiroli et al. | 549/510 |
| 2004/0049060 | A1 * | 3/2004 | Battaglia et al. | 549/510 |
| 2005/0020669 | A1 * | 1/2005 | Bombardelli et al. | 514/449 |
| 2005/0113585 | A1 * | 5/2005 | Pontiroli et al. | 549/510 |
| 2006/0122258 | A1 * | 6/2006 | Fontana et al. | 514/449 |

FOREIGN PATENT DOCUMENTS

| EP | 0 559 019 | 9/1993 |
|---|---|---|
| WO | WO 96/29321 | 9/1996 |
| WO | WO 96/30373 | 10/1996 |
| WO | WO 96/36622 | 11/1996 |
| WO | WO 97/43291 | 11/1997 |
| WO | WO 98/30553 | 7/1998 |
| WO | WO 02/12215 | 2/2002 |

* cited by examiner

*Primary Examiner*—D. Margaret Seaman
*Assistant Examiner*—Raymond Covington
(74) *Attorney, Agent, or Firm*—Young & Thompson

(57) ABSTRACT

A process for the preparation of 14β-hydroxy-baccatin III-1,14-carbonate useful for the preparation of novel taxane derivatives with antitumor activity.

10 Claims, No Drawings

PROCESS FOR THE PREPARATION OF THE 14β-HYDROXY-BACCATIN III-1,14-CARBONATE

The present invention relates to a process for the preparation of 14β-hydroxy-1,14-carbonate-baccatin III. The product obtained with the process of the invention can be used in the preparation of novel taxane derivatives with antitumor activity.

Taxanes are one of the most important classes of antitumor agents developed in recent years. Paclitaxel is a diterpene complex obtained from the bark of *Taxus brevifolia* and is considered one of the major medicaments for the therapy of cancer. At present, an extensive search is being carried out for novel taxane derivatives having superior pharmacological activity and improved pharmacokinetic profile. A specific approach relates to baccatin III derivatives variously modified with respect to the parent structure. Examples of said compounds are represented by the 14β-hydroxy baccatin III derivatives disclosed in U.S. Pat. No. 5,705,508, WO 97/43291, WO 96/36622. At present, 14β-hydroxy-deacetyl-baccatin III 1,14-carbonate derivatives are prepared starting from the precursor 14β-hydroxy-deacetylbaccatin III, which is a natural compound obtainable in small amounts by extraction of the leaves of Taxus wallichiana, as disclosed in EP 559019. There is strong need for novel processes for the easy, effective preparation of large amounts of 14β-hydroxy-1,14-carbonate-baccatin III, and hence the derivatives thereof.

It has now been found that 14β-hydroxy-baccatin III-1,14-carbonate can be prepared with a process starting from 13-ketobaccatin III, which compound can be easily obtained from 10-deacetylbaccatin III, which can in turn be easily isolated in large amounts from the leaves of *Taxus baccata*, contrary to 14β-hydroxy-baccatin III.

Therefore, the invention relates to a process for the preparation of 14β-hydroxy-baccatin III-1,14-carbonate which comprises the following steps:

a. treatment of 7-Boc-13-ketobaccatin III of formula

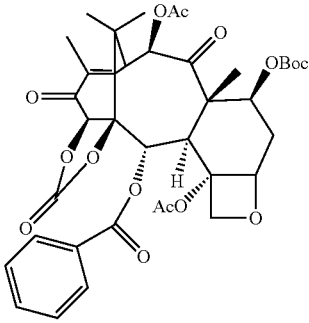

with suitable bases and oxidizing agents, to give 7-Boc-13-keto-14-hydroxy-baccatin III:

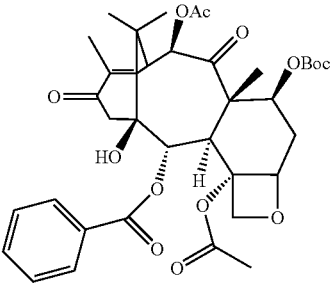

b. carbonation of the 1 and 14 hydroxy groups to give 14β-Hydroxy-7-Boc-13-keto-baccatin III-1,14-carbonate:

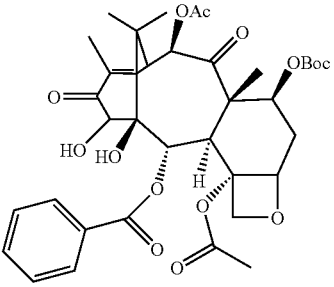

c. reduction of the ketone at the 13 position and cleavage of the protective group in 7 or vice versa.

Starting 13-ketobaccatin III is conveniently protected at the 7 position with a suitable protective group, preferably tert-butoxycarbonyl (Boc). Step a) is carried out by treatment with a suitable base, in particular potassium t-butoxide (t-BuOK) or potassium bis(trimethylsilyl)amide (KHMDS). The reaction can be carried out at −40 to −78° C. Suitable solvents for this reaction are ethers, such as tetrahydrofuran or diethyl ether, in particular in mixture with hexamethylphosphoramide (HMPA) or 1,3-dimethyl-3,4,5,6-tetrahydro-2(1H)pyrimidinone (DMPU). The enolate is then treated with an oxidizing agent, such as oxaziridine derivatives (in particular N-benzenesulfonyl phenyl oxaziridine, N-benzenesulfonyl m-nitrophenyl oxaziridine and camphorsulfonyloxaziridine) to provide the 7-protected 13-keto-14-hydroxy-baccatin III derivative.

Step b) is then carried out by treatment with a carbonylating agent (for example carbonyldiimidazole or phosgene) under the conditions usually described in literature, to provide the 1,14-carbonate derivative. The reaction can be conveniently carried out in inert solvents, preferably ethers or chlorinated solvents, in the presence of a base (preferably pyridine or triethylamine), at a temperature ranging from −40° C. to room temperature. The reaction can be carried out both on the pure starting material and on the crude from the previous step.

The reduction of the carbonyl at the 13 position of step c) is easily carried out with tetrabutylammonium borohydride in ethanol at a temperature usually ranging from −20 to −50° C., and is completed within 2-6 hours. The reaction can also be carried out in methanol, isopropanol, or in a methanol and tetrahydrofuran mixture. The reducing agent can be used in stoichiometric amount, although a hydride excess is preferably used. The reduction can also be effected with other hydrides, preferably lithium borohydride, sodium borohydride, sodium triacetoxy borohydride, in the conditions known in the technique.

Protection at the 7 position is removed under conditions depending on the protective group used. For example, if the protective group at the 7 position is tert-butoxycarbonyl, hydrolysis with formic acid can successfully be used.

The starting 13-ketobaccatin III can be readily prepared according to one of the two following procedures.

10-Deacetyl-baccatin III is selectively oxidized at the 13-position with ozone to give 13-keto-10-deacetyl baccatin III. Oxidation can be carried out in alcoholic or chlorinated solvents, in particular methanol or methylene chloride, at a temperature ranging from −78 to room temperature. 13-Keto-10-deacetyl-baccatin III is then regioselectively acetylated to give 13-keto-baccatin III.

Alternatively, 13-keto-baccatin III can be obtained by oxidation of baccatin III either natural or obtainable by regioselective acetylation of 10-deacetylbaccatin III. Oxidation can be carried out with ozone, or also with manganese dioxide in aprotic solvents such as methylene chloride, at temperatures ranging from 0° C. to 60° C., more preferably at room temperature.

The processes of the invention are summarized in the following scheme:

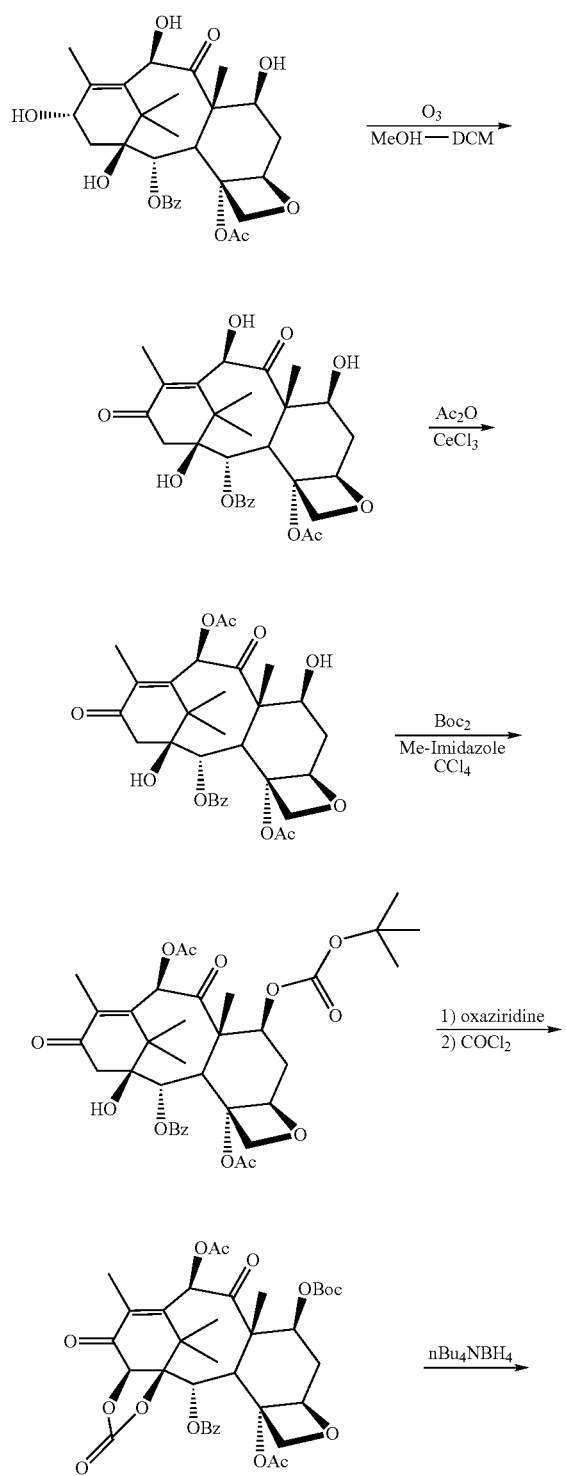

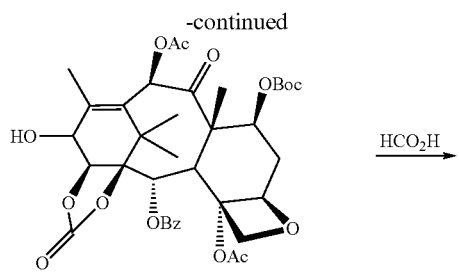

The following examples further illustrate the invention.

The abbreviations used are as follows:

AcOEt=ethyl acetate; TES=triethylsilyl; TESCl=triethylsilyl chloride; DCM=dichloromethane, THF=tetrahydrofuran, HMPA=hexamethylphosphoramide, DMPU=1,3-dimethyl-3,4,5,6-tetrahydro-2(1H)pyrimidinone.

EXAMPLE 1

10-Deacetyl-13-keto-baccatin III

10-Deacetyl-baccatin III (3 g, 5 mmol) was dissolved in DCM-MeOH 1:1 (250 ml) and cooled to −78° C. An ozone stream (1.4 g/ml) was bubbled through the solution until disappearance of the starting material (2 h). The ozone stream was replaced with nitrogen. The solution was then treated with dimethyl sulfide (1 ml) and pyridine (1 ml), the solvent was evaporated off and the crude was dissolved in EtOAc (100 ml) and washed with 0.1 N HCl and ice. After evaporating off the solvent, the title product was obtained in a 90% yield.

EXAMPLE 2

13-Keto-baccatin III

Baccatin III (150 g, 0.25 mol) was dissolved in acetone (1.43 l). Commercially available manganese dioxide (450 g) was added in three portions under strong stirring. After the starting product disappeared (4 h) the suspension was filtered and the solvent evaporated off. The crude was suspended in EtOAc (100 ml) and refluxed for 1 h, then c-Hex (100 ml) was added. The title compound was obtained from mother liquors, after evaporation of the solvent, as white solid (140 g, 95%).

EXAMPLE 3

7-Boc-13-keto-baccatin III

A solution of 13-keto-baccatin III (1.1 g, 1.9 mmol) in methylene chloride (0.5 ml) was dissolved in carbon tetrachloride (14 ml) at room temperature. 1-methylimidazole (35 ml, 0.282 mmol) and Boc$_2$O (1.026 g, 4.7 mmol) were then added under stirring strong. The solution was left under stirring at 20° C. for 18 hours. After that, the solvent was replaced with acetone (5 ml), the solution was poured into water (5 ml) and left under stirring overnight. The precipitate was collected on buchner funnel, washed with n-pentane and dried to give 1.1 g of the title product (1.78 mmol, 94%).

EXAMPLE 4

14-Hydroxy-7-Boc-13-ketobaccatin III

A solution of 7-Boc-13-keto-baccatin III (0.65 g, 0.95 mmol) in THF-DMPU 8:2 (10 ml) was added to a solution of t-BuOK (0.425 g, 3.79 mmol) in anhydrous THF (10 ml) under stirring at −60° C. After 15 minutes, a solution of camphorsulfonyloxaziridine (2.63 mmol) in THF-DMPU 8:2 (10 ml) was added. After the starting material disappeared (45 min), the reaction was quenched with glacial acetic acid (0.4 ml) and the mixture was diluted with 10% aqueous NH$_4$Cl al (25 ml). The organic layer was washed with water, dried over sodium sulfate and evaporated under reduced pressure. The product was used for the subsequent step without purification.

EXAMPLE 5

14β-Hydroxy-7-Boc-13-ketobaccatin III 1,14-carbonate

14-Hydroxy-7-Boc-13-ketobaccatin III (2.0 g) and carbonyldiimidazole (0.65 g, 4.0 mmol) were dissolved in toluene (11 ml) and heated at 75° C. under stirring for 90 min. The solution was cooled to room temperature and treated with 0.2 N HCl (5 ml). The organic layer was diluted with EtOAc (15 ml), washed with water, dried, and the solvent was evaporated off. The title compound was obtained by flash-chromatography (silica gel, cHex/DCM/Et$_2$O, 14:3.5:2.5) as a white solid (0.87 g, 1.20 mmol, 82% on two steps).

EXAMPLE 6

14β-Hydroxy-7-Boc-baccatin III 1,14-carbonate

A solution of 14β-Hydroxy -7-Boc-13-ketobaccatin III 1,14-carbonate in THF (3 ml) was added to a solution of tetrabutylammonium borohydride (1.29 g) in dry methanol (11 ml) at −50° C. under inert atmosphere. After 4 hours the reaction was quenched with a solution of citric acid (1.5 g) in water (5 ml). The mixture was extracted with ethyl acetate. The organic phase was dried over magnesium sulfate and evaporated under reduced pressure. The crude was purified by column chromatography to give 14β-Hydroxy-7-Boc-baccatin III 1,14-carbonate (68%) and 13-epi-14β-Hydroxy -7-Boc-baccatin III 1,14-carbonate (28%) in a 70% conversion yield.

EXAMPLE 7

14β-Hydroxy-baccatin III 1,14-carbonate

A 97% formic acid solution (5 ml) was added to a solution 14β-Hydroxy-7-Boc-baccatin III 1,14-carbonate (0.50 g, 0.68 mol) in dichloromethane (3 ml) at −8° C. The reaction was kept under stirring for 5 days, then neutralized with 2N ammonia. The organic phase was extracted with ethyl acetate, dried and evaporated under reduced pressure. Silica gel chromatography (hexane-ethyl acetate=1.0:1.3) afforded the product as a white solid in a 65% yield.

The invention claimed is:

1. A process for the preparation of 14β-hydroxy--1,14-carbonate-baccatin III, which comprises:

a) treatment of 7-Boc-13-ketobaccatin III of formula

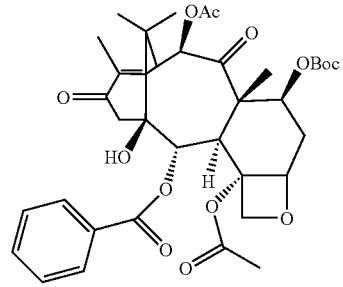

with suitable bases and oxaziridine compounds as oxidizing agents, to give 7-Boc-13-keto-14-hydroxy-baccatin III:

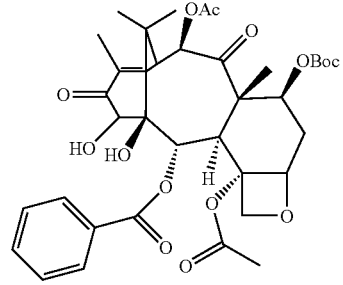

b) carbonation of the 1 and 14 hydroxy groups to have 14β-Hydroxy-7-Boc-13-keto-baccatin III-1,14-carbonate:

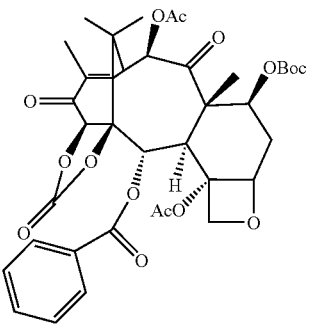

c) reduction of the ketone at the 13 position and cleavage of the protective group in 7.

2. The process as claimed in claim 1, wherein step a) is carried out by treatment with potassium t-butoxide or potassium bis(trimethylsilyl)amide at a temperature from -40 to -78° C. in ethers in mixture with hexamethylphosphoramide (HMPA) or 1, 3-dimethyl-3,4,5, 6-tetrahydro-2(1H)pyrimidinone (DMPU), in the presence of oxaziridine compounds.

3. The process as claimed in claim 1, wherein step b) is carried out by treatment with a carbonyldiimidazole or phosgene in chlorinated solvents in the presence of a base at temperatures ranging from -40° C. to room temperature.

4. The process as claimed in claim 1, wherein step c) is carried out by treatment with a hydride at a temperature from -20 to -50° C.

5. The process as claimed in claim 4 wherein the hydride is selected from the group consisting of tetrabutylammonium borohydride, tetraethylammonium borohydride, sodium borohydride, lithium borohydride, and sodium triacetoxy borohydride, and wherein the reaction is carried out in ethanol, methanol, isopropanol, or in a methanol and tetrahydrofuran mixture.

6. The process as claimed in claim 1, wherein 13-keto-baccatin III protected at the hydroxyl in 7 is prepared by selective acetylation of the hydroxyl 10 followed by oxidation of the hydroxyl 13 and protection of the hydroxyl 7.

7. The process as claimed in claim 6, wherein 13-keto-baccatin III is obtained by selective acetylation of deacetyl-baccatin III in 10 with acetic anhydride followed, by oxidation with manganese dioxide in aprotic solvents at 0° C.-60° C. or by oxidation of baccatin III with ozone.

8. An intermediate compound 7-Boc-13-keto-14-hydroxy--baccatin III, of formula

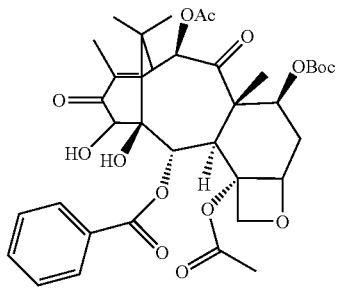

9. An intermediate compound 14β-Hydroxy-7-Boc-13-keto-baccatin III-1,14-carbonate, of formula:

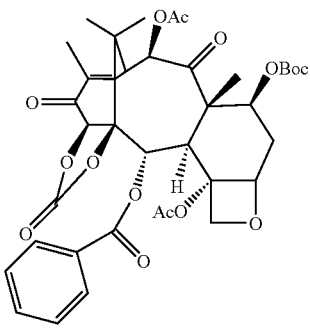

10. An intermediate compound 14β-Hydroxy-7-Boc-13-hydroxy-baccatin III-1,14-carbonate, of formula:

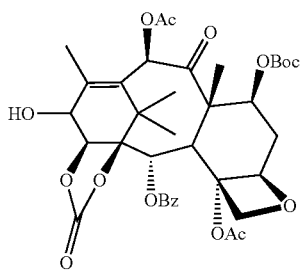

* * * * *